United States Patent [19]

McNeil et al.

[11] Patent Number: 4,828,546
[45] Date of Patent: May 9, 1989

[54] BULB EVACUATOR FOR CLOSED WOUND SUCTION

[75] Inventors: Charles B. McNeil, Wayzata; Thomas J. McEvoy, Minnetonka; Jeffery D. Dahlquist, Anoka, all of Minn.

[73] Assignee: Surgidyne, Inc., Eden Prairie, Minn.

[21] Appl. No.: 87,809

[22] Filed: Aug. 21, 1987

[51] Int. Cl.$^4$ ............................................. A61M 1/00
[52] U.S. Cl. ..................................... 604/73; 604/133; 604/212; 604/213; 604/319
[58] Field of Search ............... 604/133, 35, 37, 73, 604/212, 213, 319

[56] References Cited

U.S. PATENT DOCUMENTS

| | | | |
|---|---|---|---|
| 4,392,858 | 7/1983 | George et al. | 604/133 |
| 4,493,701 | 1/1985 | Bootman et al. | 604/133 |
| 4,551,141 | 11/1985 | McNeil | 604/319 |
| 4,664,652 | 5/1987 | Weilbacher | 604/133 |

FOREIGN PATENT DOCUMENTS 1222961  6/1960  France ................................. 604/37

Primary Examiner—Albert W. Davis, Jr.
Attorney, Agent, or Firm—Larson & Taylor

[57] ABSTRACT

A bulb evacuator is provided for closed wound suction having a flexible compressible container with a pair of inlets having one way valves therein and a port to a suction source with a removable cap thereon at one end of the bulb evacuator. The opposite end of the bulb evacuator is provided with an integrally formed anti-reflux valve and a latching device surrounding the anti-reflux valve. A separate collection bag can be attached to the latching device so that when the bulb evacuator is filled with fluid from a closed wound, it can be compressed to force the fluid into the attached collection chamber and simultaneously creating a suction within the bulb evacuator to promote further withdrawal of fluids from the closed wound.

6 Claims, 3 Drawing Sheets

BULB EVACUATOR FOR CLOSED WOUND SUCTION

FIELD OF THE INVENTION

The present invention relates to a bulb evacuator for collecting fluids from a closed wound. The bulb evacuator includes two ports for evacuating fluid from two different sites of the wound and is also provided with a port for direct connection to suction tubing connected to a separate suction source to provide suction apart from the suction created when the flexible bulb is evacuated. The bulb evacuator has a one way anti-reflux valve in an end thereof and is provided with means for attaching a separate flexible collection chamber to receive fluids evacuated from the bulb evacuator.

BACKGROUND OF THE INVENTION

There are numerous closed wound suction devices presently available on the market. Such devices all have in common a chamber which may be evacuated by compression or otherwise and an inlet to which a tube is attached and which extends to the closed wound which is to be drained. Certain of the prior art closed wound suction devices also are provided with a separate collection bag so that the evacuating device can be drained when needed. For example, U.S. Pat. No. 4,392,857 discloses a wound drainage device including inlet and outlet ports so that fluid drained into the resilient squeeze bulb may be forced outwardly into a separate storage bag.

While the prior art devices disclose certain of the features of the present invention, such closed wound suction devices do not have the adaptability or ease of operation provided by the present invention.

SUMMARY OF THE INVENTION

The bulb evacuator for closed wound suction according to the present invention provides a flexible compressible bulb having a semirigid cap on one end thereof having a pair of inlet ports extending through the cap. Each inlet port has a one way valve therein to permit passage of fluid into the bulb but to prevent fluid flow from the bulb into the inlet passageway. One of the inlet passageways is provided with a closure which may be cut off when it is necessary to withdraw fluid from two sites in the wound. The cap is also provided with a separate suction port having a removable closure thereon so that, if desired, wall suction or other auxiliary suction source can be applied to the bulb and to the patient closed wound.

The opposite end of the bulb evacuator has an anti-reflux valve integrally formed with the bulb evacuator. A connector surrounds the anti-reflux valve on the outside of the bulb and a combination cap and latch is secured to the connector. A separate collection bag such as shown in U.S. Pat. No. 4,551,141 issued Nov. 5, 1985, may be latched onto the bulb evacuator in fluid communication with the anti-reflux valve so that when the bulb evacuator is squeezed to displace fluid contained in the bulb evacuator, it passes through the anti-reflux valve and into the separate collection chamber. The bulb may be squeezed until it is completely evacuated and the bulb anti-reflux valve prevents the fluid from re-entering the bulb and prevents sucking in air into the bulb and maintains the bulb in a collapsed suction activated state so that only fluid entering the bulb from the closed wound drain will allow the bulb to expand. The collection bag is then removed from the bulb evacuator and capped for disposal. A sterile replacement collection bag is then attached to the collapsed bulb which has remained collapsed due to the anti-reflux valve in the bulb. During the replacement procedure the anti-reflux valve also helps prevent exogenous bacteria that are in the air from being sucked back into the unit. Thus, according to the present invention a completely closed system is provided for removing fluids from a closed wound and passing the fluids into a bulb evacuator and for reusing the bulb evacuator by displacing the fluids collected from the bulb evacuator into a separate collection bag.

An object of the present invention is to provide a closed wound suction device which includes a bulb evacuator having an anti-reflux valve integrally formed therein together with means for collecting fluids from the bulb evacuator.

Another object of the present invention is to provide a bulb evacuator with one end having dual inlet ports with one way valves disposed therein, together with a suction port adapted to be connected to a separate suction source and the opposite end having an outlet port with means for latching a separate collection chamber onto the bulb evacuator.

Other objects and many of the intended advantages of the present invention will become more readily apparent upon consideration of the following detailed specification in connection with the accompanying drawings.

BRIEF DESCRIPTION OF THE DRAWINGS

FIG. 6 is a sectional view through the outlet portion of the bulb evacuator housing and FIG. 7 is an elevational view partially in section showing a collection bag attached to the outlet of the bulb evacuator.

DETAILED DESCRIPTION OF THE PREFERRED EMBODIMENT

Figure 1:
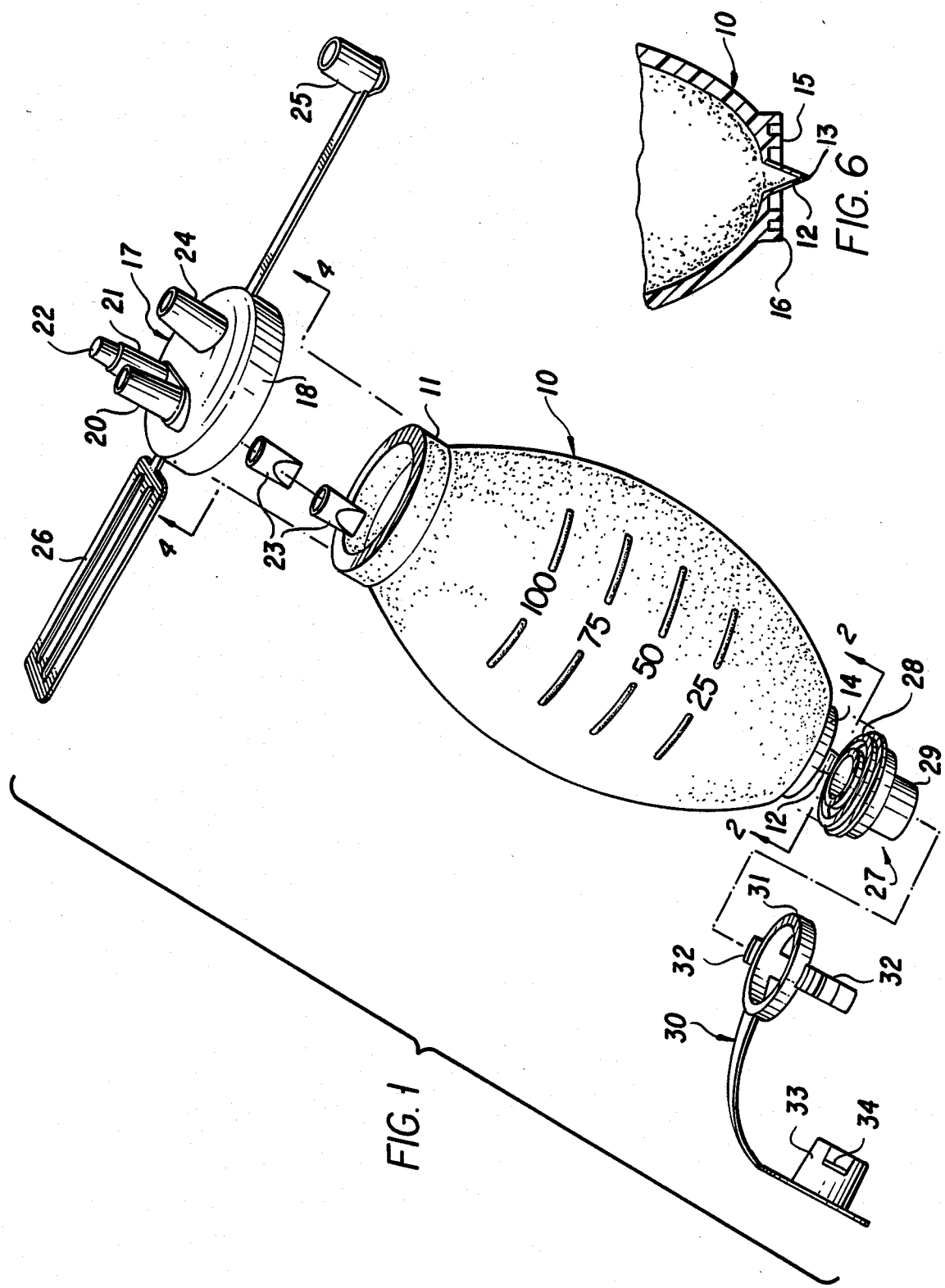
FIG. 1 is an exploded perspective view showing the various elements of the bulb evacuator.
Figure 2:
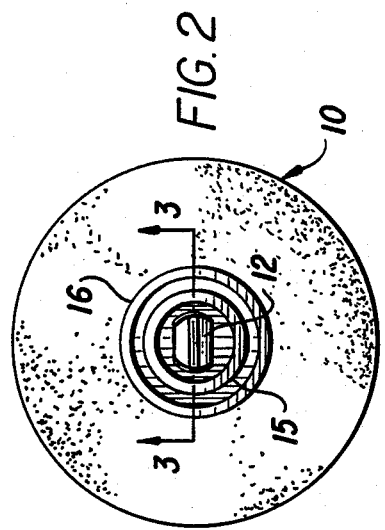
FIG. 2 is a view of the outlet end of the end of the bulb evacuator taken along the line 2—2 of FIG. 1.
Figure 3:
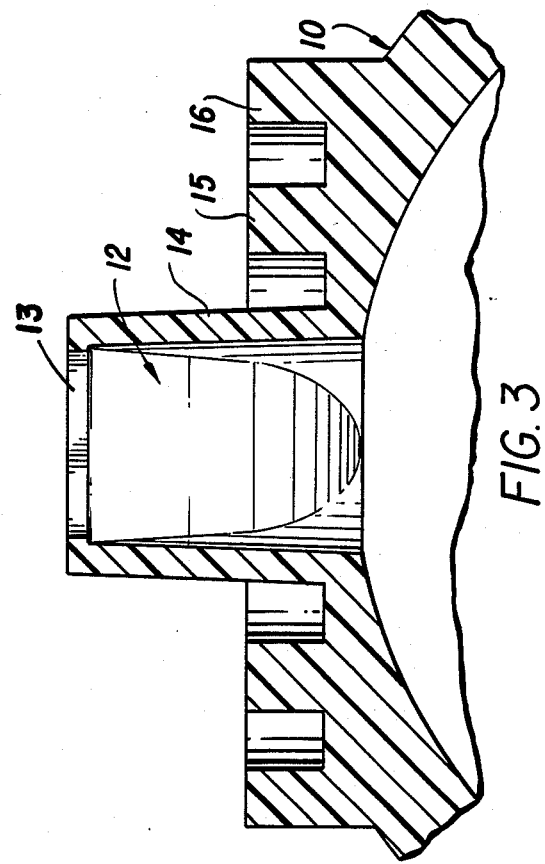
FIG. 3 is a sectional view of the outlet end of the bulb evacuator along the line 3—3 of FIG. 2.

With reference now to the drawings in which like numerals indicate like elements throughout the several views, a presently preferred embodiment of the bulb evacuator is depicted in detail in FIG. 1. There is provided a flexible bulb 10 which is generally ellipsoidal in shape and which may be made of a material such as polyvinyl chloride medical grade or silicone rubber. The material used is translucent so that the contents may be viewed. The inlet end of the bulb evacuator is formed with a circular opening having an enlarged circular flange 11 surrounding the opening. The opposite end of the bulb evacuator 10 is provided with an integral anti-reflux valve 12 as shown in FIGS. 3 and 6. The anti-reflux valve 12 is formed of the same material as the bulb evacuator but with relatively thin walls. The walls are shown in section at 14. A slit 13 extends across the outer end of the anti-reflux valve 12 and the valve will only open in response to pressure from within the bulb evacuator to force the slit 13 to an open position in opposition to the resiliency of the material holding the slit in a closed position. A pair of circular concentric bosses 15 and 16 surround the anti-reflux valve 12.

Figure 4:
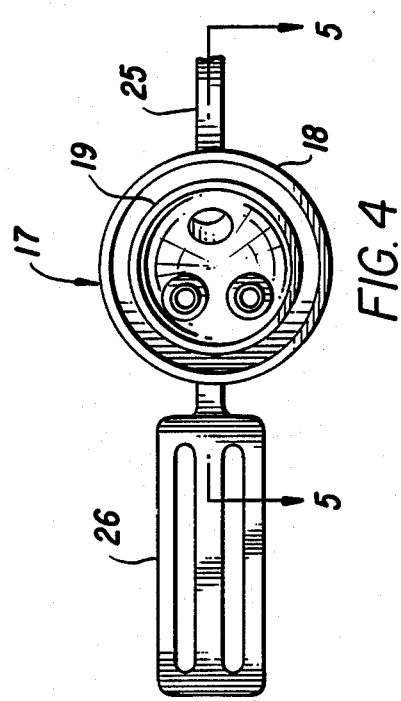
FIG. 4 is a plan view of the inlet cap of the bulb evacuator along the line 4—4 of FIG. 1.
Figure 5:
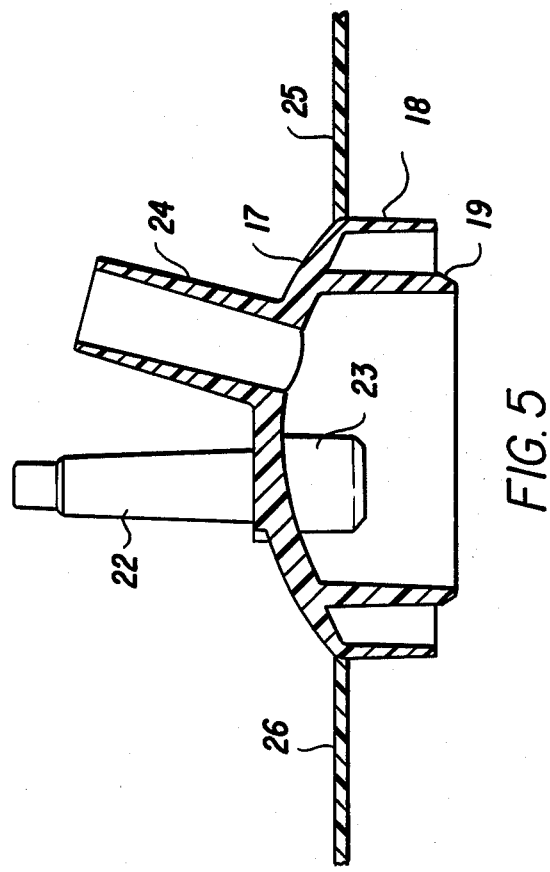
FIG. 5 is a sectional view of the cap along the lines 5—5 of FIG. 4.

The cap 17 as seen in FIGS. 1, 4 and 5 may be formed of a semirigid plastic material such as, for example, polyvinyl chloride. The cap 17 has integrally formed spaced circular flanges 18 and 19 formed thereon as seen in FIGS. 4 and 5. When assembled the flange 19 fits inside the flange 11 of the bulb evacuator 10 and the flange 18 fits around the outer side of the flange 18. The cap member may be bonded to the bulb by any convenient bonding material such as cyclohexanone. The cap 17 has a pair of inlet passageways 20 and 21 extending from the outer face thereof as shown in FIG. 1. Inlet passageway 21 has a cover member 22 formed integrally therewith which may be cut off when it is necessary to use two inlet ports. Each port has a one way valve 23 which is secured onto each of the inlet passageways. These inlet valves permit fluid flow from outside the cap 17 into the interior of the bulb evacuator 10 but will not permit fluid to flow from inside the bulb evacuator through the passageways 20 and 21.

The cap 17 is also provided with a separate port 24 which may be connected to wall suction within a hospital or to a separate suction pump. Port 24 is tapered to fit commonly employed suction tubings with funnel shaped ends or molded connectors. Formed integrally with the cap 17 is a removable closure 25 for the suction port 24 which can be readily removed should the additional suction become necessary. There is also provided a strap 26 having slots therein which may be used to attach the bulb evacuator to the patient.

Figure 7:
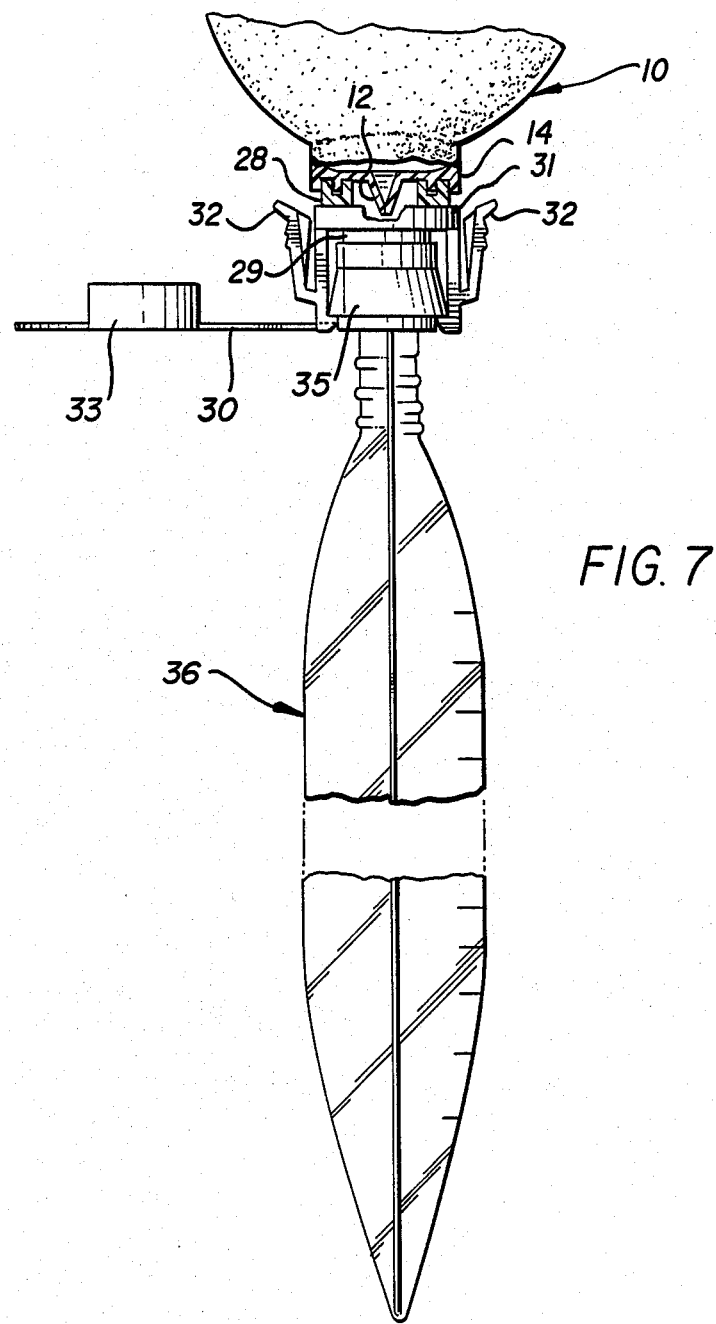

The outlet end of the bulb evacuator has, as noted hereinbefore, an integrally formed anti-reflux valve 12 therein. This anti-reflux valve provides for simultaneous emptying of the bulb evacuator and also for reactivation of the suction within the bulb since the anti-reflux valve 12 only permits fluid flow from inside the bulb through the slit 13. A connector 27, as shown in FIG. 1, is provided and this connector has a circular boss 28 thereon which extends into the circular recess formed between the circular bosses 15 and 16 on the outlet end of the bulb evacuator 10. The connector 27 is bonded to the bulb in any suitable manner. The connector 27 has a tubular sleeve 29 which surrounds the anti-reflux valve 12 of the bulb 10. The lumen of sleeve 29 is stepped to mate to the connector 35 of the collection bag 36 as shown in FIG. 7 to provide a flush fitment and thereby prevent fluid entrapment within the sleeve during the transfer of fluid from the bulb to the collection bag.

A latching device 30 is provided which comprises a latching ring 31 having a pair of resilient latching elements 32 which form releasable locking means extending at right angles with respect to the plane of the latching ring 31. A cap or removable cover 33 is integrally formed with the latching device 30. In use the latching ring 31 extends around the sleeve 29 and is bonded to the connector 27. The cap 33 fits over the end of the sleeve 29 and locking projections 34 on the cap 33 cooperate with the resilient latching elements 32 to retain the cover in place. These same latching elements 32 engage the connector 35 on collection bag 36 to retain the collection bag on the outlet of the bulb evacuator as shown in FIG. 7.

In the most common configuration of use of the bulb system, the collection bag is attached to the outlet end of the bulb evacuator, the drain tube is placed into the patient wound in the area to be drained and the drain is connected to the syringe access port connection device which is then connected to the inlet port 20 of the bulb. If two inlets are to be used, the cover 22 of the inlet tube 21 is cut off and an additional drain and syringe access port connection device are attached to inlet 21. If suction is desired during wound closure, suction port 24 is connected to suction tubing and then to the auxiliary suction source such as wall suction or an electrical pump. When wound closure is complete, the bulb is compressed with suction port 24 open to expel the air, and then sealed with port closure 25. Upon release of the bulb, suction is created within the bulb which served to drain the closed wound.

Fluid from the closed wound flows through the drain tubes and inlets 20 and 21, through the one-way valve 23 and into the bulb 10. When emptying and reactivation of the bulb is desired, the collection bag as shown in U.S. Pat. No. 4,551,141 is unrolled, the bulb is compressed to expel the contents from the bulb through the anti-reflux valve 20 and into the collection bag. The collection bag is then removed by releasing the latches through the tube, capped for measurement and disposal. The sterile replacement collection bag is placed onto the sleeve of the bulb. A bulb will remain in the collapsed state during the removal and replacement of the collection bag due to the anti-reflux valve 12. The anti-reflux valve 12 prevents the reflux of air from the outside back into the bulb when the bulb is being emptied even if the user temporarily releases the bulb. The user is able to squeeze the unit until it completely evacuated and the bulb anti-reflux valve prevents it from rebounding and sucking in air or fluid which may contain exogenous bacteria. The anti-reflux valve also prevents exogenous bacteria that are in the air from being sucked back into the bulb. The use of the presently disclosed bulb evacuator in conjunction with the separate collection chamber disclosed in U.S. Pat. No. 4,551,141 provides a completely closed system for emptying, collecting, measuring and disposal of the exudate from the bulb evacuator.

Obviously many modifications and variations of the present invention are possible in light of the above teachings.

What is claimed as new and is desired to be secured by Letters Patent is:

1. A bulb evacuator for closed wound suction comprising a flexible bulb, a cap on one end of said bulb, at least one inlet passageway in said cap for connecting the interior of said bulb with a closed wound, one way valve means in said inlet passageway for permitting fluid flow into said bulb, an outlet passageway in said cap for connecting the interior of said bulb with a suction source, removable closure means for said outlet passageway, a one way valve disposed in the opposite end of said bulb for permitting fluid flow from said bulb, and means on said opposite end of said bulb for attaching a collection bag to said bulb, said last named means including a tubular outlet passageway surrounding said last named one way valve, a removable cover for said passageway and releasable locking means for retaining the removable cover over the outlet passageway to close the passageway and for retaining a collection bag on the outlet passageway when the cover is removed.

2. A bulb evacuator according to claim 1 and further including a second inlet passageway in said cap, said second inlet passageway having an integral closure thereon, said closure being formed of thinner plastic material than said passageway whereby said closure may be cut off when use of said second inlet passageway is required.

3. A bulb evacuator according to claim 2 and further including a one way valve in said second inlet passageway for permitting fluid flow into said bulb.

4. A bulb evacuator according to claim 1 wherein said one way valve disposed on the opposite end of said bulb is formed integrally with said bulb and comprises a pair of lips of thin flexible plastic material with a slit therebetween extending outwardly from the opposite end of said bulb.

5. A bulb evacuator according to claim 1 wherein said cap includes a pair of circular spaced inwardly extending flanges to engage the inner and outer faces of the open one end of said bulb.

6. A bulb evacuator according to claim 1 wherein said one way valve disposed in the opposite end of said bulb is integrally formed with the flexible bulb.

* * * * *